United States Patent
Lee et al.

(10) Patent No.: US 10,174,055 B2
(45) Date of Patent: Jan. 8, 2019

(54) SYNTHETIC METHOD OF FUSED HETEROAROMATIC COMPOUND AND FUSED HETEROAROMATIC COMPOUND AND INTERMEDIATE THEREFOR

(71) Applicant: Samsung Electronics Co., Ltd., Suwon-si, Gyeonggi-do (KR)

(72) Inventors: Don-Wook Lee, Seoul (KR); Jeong Il Park, Seongnam-si (KR); Eigo Miyazaki, Hwaseong-si (KR)

(73) Assignee: Samsung Electronics Co., ltd., Gyeonggi-Do (KR)

( * ) Notice: Subject to any disclaimer, the term of this patent is extended or adjusted under 35 U.S.C. 154(b) by 0 days.

(21) Appl. No.: 15/904,677

(22) Filed: Feb. 26, 2018

(65) Prior Publication Data
US 2018/0179227 A1    Jun. 28, 2018

Related U.S. Application Data

(62) Division of application No. 15/332,186, filed on Oct. 24, 2016, now Pat. No. 9,932,357.

(30) Foreign Application Priority Data

Jun. 14, 2016  (KR) .................. 10-2016-0073947

(51) Int. Cl.
| | |
|---|---|
| C07D 517/22 | (2006.01) |
| H01L 51/00 | (2006.01) |
| C07D 495/04 | (2006.01) |
| H01L 51/05 | (2006.01) |

(52) U.S. Cl.
CPC .......... C07D 517/22 (2013.01); C07D 495/04 (2013.01); H01L 51/0071 (2013.01); H01L 51/0558 (2013.01)

(58) Field of Classification Search
CPC .................................................. C07D 517/22
USPC .......................................................... 549/50
See application file for complete search history.

(56) References Cited

U.S. PATENT DOCUMENTS

| 7,816,673 B2 | 10/2010 | Park et al. |
| 2013/0320316 A1 | 12/2013 | Park et al. |

FOREIGN PATENT DOCUMENTS

| JP | 2006290192 A | 10/2006 |
| KR | 20100118253 A | 11/2010 |
| KR | 2013-0136938 A | 12/2013 |
| WO | WO-20090009790 A1 | 1/2009 |
| WO | WO-2013159863 A1 | 10/2013 |

OTHER PUBLICATIONS

Jeong-Il Park et al. "Dibenzothiopheno[6,5-b:6'5'-f]thieno[3,2-b]thiophene (DBTTT): High-Performance Small-Molecule Organic Semiconductor for Field-Effect Transistors". JACS: Journal of the American Chemical Society. ACS Publications—American Chemical Society. 2015. pp. 12175-12178.

*Primary Examiner* — Taofiq A Solola
(74) *Attorney, Agent, or Firm* — Harness, Dickey & Pierce, P.L.C.

(57) ABSTRACT

A synthetic method of a fused heteroaromatic compound includes preparing a first intermediate represented by Chemical Formula 1, obtaining a second intermediate by reacting the first intermediate and an aldehyde compound, obtain a third intermediate by performing deprotection and reduction reactions on the second intermediate, and obtaining a fused heteroaromatic compound by performing a cyclization reaction on the third intermediate.

2 Claims, 1 Drawing Sheet

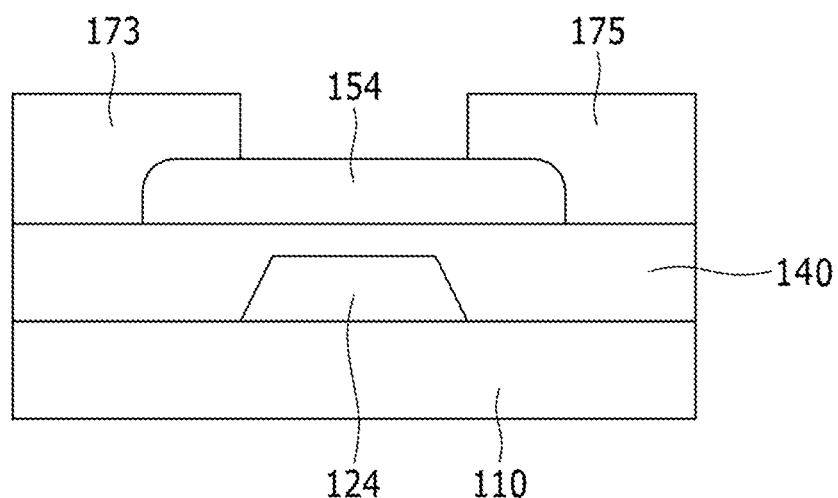

SYNTHETIC METHOD OF FUSED HETEROAROMATIC COMPOUND AND FUSED HETEROAROMATIC COMPOUND AND INTERMEDIATE THEREFOR

CROSS-REFERENCE TO RELATED APPLICATION

This is a divisional application of U.S. application Ser. No. 15/332,186, which claims priority to and the benefit of Korean Patent Application No. 10-2016-0073947 filed in the Korean Intellectual Property Office on Jun. 14, 2016, the entire contents of which are incorporated herein by reference.

BACKGROUND

1. Field

Example embodiments provide a synthetic method of a fused heteroaromatic compound, a fused heteroaromatic compound, and an intermediate therefor.

2. Description of the Related Art

A flat panel display (e.g., a liquid crystal display (LCD) or an organic light emitting diode (OLED) display) includes a thin film transistor (TFT) that is a three-terminal element as a switch. Research on an organic thin film transistor (OTFT) including an organic semiconductor (e.g., a low molecular semiconductor or polymer semiconductor) instead of an inorganic semiconductor (e.g., a silicon (Si) semiconductor) as one type of thin film transistor is being actively conducted. The organic thin film transistor may be made into a fiber or a film due to characteristics of an organic material, and thus is drawing attention as a core element for a flexible display device. The organic thin film transistor may be manufactured using a solution process (e.g., inkjet printing), and may be more easily applied to a large area flat panel display where a deposition process has a limit.

SUMMARY

Example embodiments provide a synthetic method of a fused heteroaromatic compound that is applicable as an organic semiconductor.

Example embodiments also provide an intermediate of the fused heteroaromatic compound.

Example embodiments also provide a fused heteroaromatic compound prepared by the method.

Example embodiments also provide an electronic device including the fused heteroaromatic compound.

According to example embodiments, a synthetic method of a fused heteroaromatic compound includes preparing a first intermediate represented by Chemical Formula 1, obtaining a second intermediate by reacting the first intermediate and an aldehyde compound, obtaining a third intermediate by performing deprotection and reduction reactions on the second intermediate, and obtaining a fused heteroaromatic compound by performing a cyclization reaction on the third intermediate.

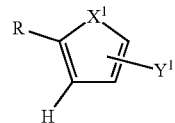

[Chemical Formula 1]

In Chemical Formula 1, $X^1$ is O, S, Se, or Te, $Y^1$ is hydrogen or a halogen, and R is a protective group.

The aldehyde compound may be represented by Chemical Formula 2 or 3.

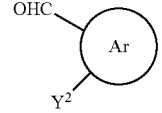

[Chemical Formula 2]

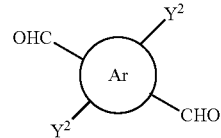

[Chemical Formula 3]

In Chemical Formulae 2 and 3,

Ar is one of a substituted or unsubstituted aromatic ring, a substituted or unsubstituted heteroaromatic ring, and a fused ring of the foregoing two or more rings, and $Y^2$ is hydrogen or halogen, provided that one of $Y^1$ and $Y^2$ is a halogen and the other of $Y^1$ and $Y^2$ is hydrogen.

The Ar may be one of benzene, thiophene, selenophene, tellurophene, furan, pyrrole, and a fused ring of the foregoing two or more rings.

Obtaining the second intermediate may further include a dehydration reaction.

The protective group may be a silicon (Si)-containing group.

The protective group may be a substituted or unsubstituted silyl group.

The protective group may be a trimethylsilyl group, a triethylsilyl group, an isopropyldimethylsilyl group, a diethylisopropylsilyl group, a t-butyldimethylsilyl group, a t-butyldiphenylsilyl group, or a triisopropylsilyl group.

Obtaining the third intermediate may include performing the deprotection reaction using a fluorine-containing compound.

Obtaining the third intermediate may include obtaining a nitrile compound from the second intermediate and performing the deprotection and reduction reactions on the nitrile compound.

Obtaining the fused heteroaromatic compound may include performing the cyclization reaction may including supplying an acidic catalyst.

The second intermediate may be represented by Chemical Formula 4 or 5.

[Chemical Formula 4]

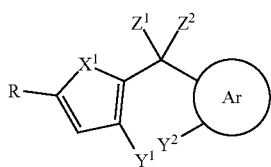

[Chemical Formula 5]

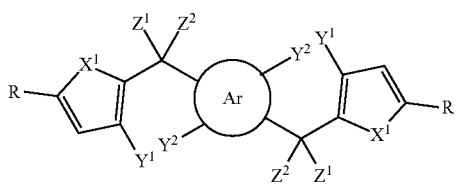

In Chemical Formulae 4 and 5,

Ar is one of a substituted or unsubstituted aromatic ring, a substituted or unsubstituted heteroaromatic ring, and a fused ring of the foregoing two or more rings, $X^1$ is O, S, Se, or Te, each of $Y^1$ and $Y^2$ is hydrogen or halogen, provided that one of $Y^1$ and $Y^2$ is a halogen and the other of $Y^1$ and $Y^2$ is hydrogen, each of $Z^1$ and $Z^2$ are hydrogen or a hydroxy group, and R is a protective group.

The fused heteroaromatic compound may have an unsubstituted terminal end.

The fused heteroaromatic compound may be represented by Chemical Formula 7 or 8.

[Chemical Formula 7]

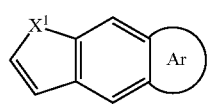

[Chemical Formula 8]

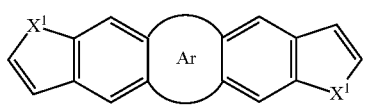

In Chemical Formulae 7 and 8,

Ar is one of a substituted or unsubstituted aromatic ring, a substituted or unsubstituted heteroaromatic ring, and a fused ring of the foregoing two or more rings, and $X^1$ is O, S, Se, or Te.

According to example embodiments, an intermediate is represented by Chemical Formula 4 or 5.

[Chemical Formula 4]

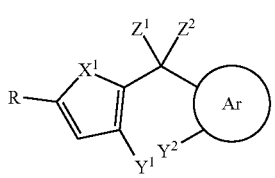

[Chemical Formula 5]

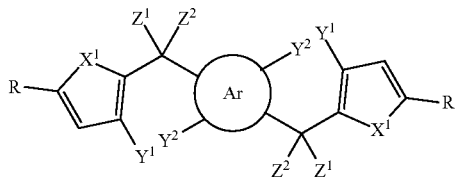

In Chemical Formulae 4 and 5,

Ar is one of a substituted or unsubstituted aromatic ring, a substituted or unsubstituted heteroaromatic ring, and a fused ring of the foregoing two or more rings, $X^1$ is O, S, Se, or Te, each of $Y^1$ and $Y^2$ is hydrogen or halogen, provided that one of $Y^1$ and $Y^2$ is a halogen and the other of $Y^1$ and $Y^2$ is hydrogen, each of $Z^1$ and $Z^2$ are hydrogen or a hydroxy group, and R is a protective group.

The Ar may be one of benzene, thiophene, selenophene, tellurophene, furan, pyrrole, and a fused ring of the foregoing two or more rings.

The protective group may be a silicon (Si)-containing group.

The protective group may be a substituted or unsubstituted silyl group.

The protective group may be a trimethylsilyl group, a triethylsilyl group, an isopropyldimethylsilyl group, a diethylisopropylsilyl group, a t-butyldimethylsilyl group, a t-butyldiphenylsilyl group, or a triisopropylsilyl group.

According to example embodiments, a fused heteroaromatic compound is prepared by the method of example embodiments.

According to example embodiments, an electronic device includes the fused heteroaromatic compound.

BRIEF DESCRIPTION OF THE DRAWING

FIG. 1 is a cross-sectional view of an organic thin film transistor according to example embodiments.

DETAILED DESCRIPTION

Example embodiments will hereinafter be described in detail, and may be more easily performed by those who have common knowledge in the related art. However, this disclosure may be embodied in many different forms and is not to be construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term 'substituted' refers to replacement by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{30}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_3$ to $C_{30}$ heterocycloalkyl group, and a combination thereof, instead of hydrogen of a compound.

As used herein, when a definition is not otherwise provided, the term "hetero" refers to one including 1 to 4 heteroatoms selected from N, O, S, Se, Te, Si, and P.

Hereinafter, a synthetic method of a fused heteroaromatic compound according to example embodiments is described.

In a synthetic method of a fused heteroaromatic compound according to example embodiments, an intermediate is obtained with a relatively high yield, and a fused heteroaromatic compound having a chalcogen element and an unsubstituted terminal end may be obtained from the novel intermediate.

A synthetic method of a fused heteroaromatic compound according to example embodiments includes preparing first intermediate that is a chalcogen cyclic compound substituted with a protective group, obtaining a second intermediate from a reaction between the first intermediate and an aldehyde compound, obtaining a third intermediate by performing deprotection and reduction reactions of the second intermediate, and obtaining a fused heteroaromatic compound by a cyclization reaction on the third intermediate.

The first intermediate may be, for example obtained by halogenating thiophene, selenophene, furan, or tellurophene to prepare a halogen-substituted thiophene, halogen-substituted selenophene, halogen-substituted furan, or halogen-substituted tellurophen and then replacing one of halogens by a protective group.

The first intermediate may be for example represented by Chemical Formula

[Chemical Formula 1]

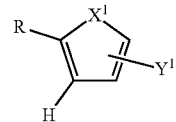

In Chemical Formula 1, $X^1$ is O, S, Se, or Te, $Y^1$ is hydrogen or a halogen, and R is a protective group.

The protective group may be boned at a position of No. 2 of thiophene, selenophene, furan, or tellurophene, and thus the position of No. 2 of thiophene, selenophene, furan, or tellurophene may suppress a chemical reaction with other compounds in the subsequent step. Particularly, the position of No. 2 of thiophene, selenophene, furan, or tellurophene may suppress a coupling reaction with an aldehyde compound, which will be described later. In addition, the protective group is easily removed in the final synthesis step to realize a fused heteroaromatic compound having the unsubstituted thiophene, selenophene, furan, or tellurophene at the terminal end. Particularly, the fused heteroaromatic compound having unsubstituted selenophene at the terminal end, which is limited in a conventional method, may be easily obtained.

The protective group may be any protective group used to suppress an organic reaction without a particular limit. The protective group may be, for example a silicon (Si)-containing group, for example a substituted or unsubstituted silyl group, but is not limited thereto. The protective group may be, for example a trimethylsilyl group, a triethylsilyl group, an isopropyldimethylsilyl group, a diethylisopropylsilyl group, a t-butyldimethylsilyl group, a t-butyldiphenylsilyl group, or a triisopropylsilyl group, but is not limited thereto.

The first intermediate may be, for example, nucleophilic addition-reacted and selectively dehydration-reacted with an aldehyde compound to obtain a second intermediate.

The aldehyde compound may be for example represented by Chemical Formula 2 or 3.

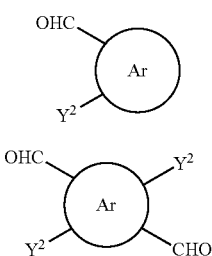

[Chemical Formula 2]

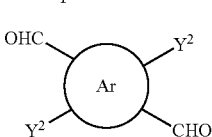

[Chemical Formula 3]

In Chemical Formulae 2 and 3,

Ar may be one of a substituted or unsubstituted aromatic ring, a substituted or unsubstituted heteroaromatic ring, and a fused ring of the foregoing two or more rings, for example benzene, thiophene, selenophene, tellurophene, furan, pyrrole, and a fused ring of the foregoing two or more rings, and $Y^2$ is hydrogen or halogen, provided that one of $Y^1$ and $Y^2$ is a halogen and the other of $Y^1$ and $Y^2$ is hydrogen.

The second intermediate may be for example represented by Chemical Formula 4 or 5.

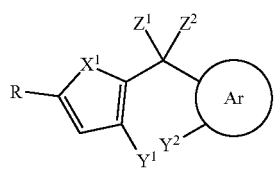

[Chemical Formula 4]

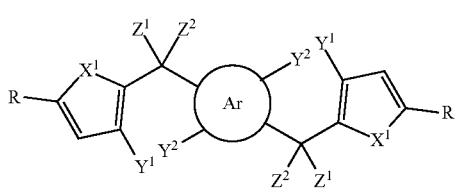

[Chemical Formula 5]

In Chemical Formulae 4 and 5,

Ar may be one of a substituted or unsubstituted aromatic ring, a substituted or unsubstituted heteroaromatic ring, and a fused ring of the foregoing two or more rings, for example benzene, thiophene, selenophene, tellurophene, furan, pyrrole, and a fused ring of the foregoing two or more rings, $X^1$ is O, S, Se, or Te, each of $Y^1$ and $Y^2$ is hydrogen or halogen, provided that one of $Y^1$ and $Y^2$ is a halogen and the other of $Y^1$ and $Y^2$ is hydrogen, each of $Z^1$ and $Z^2$ are hydrogen or a hydroxy group, and R is a protective group.

The second intermediate may be, for example, reacted with a metal cyanide compound to obtain a nitrile compound, and the nitrile compound may be deprotection-reacted to remove the protective group and to obtain a third intermediate. Accordingly, the third intermediate may have the unsubstituted thiophene, selenophene, furan, or tellurophene at the terminal end.

The deprotection reaction may be, for example, performed by using a compound including fluorine, for example, using tetrabutylammonium fluoride, triethylamine trihydrofluoride, hydrofluoric acid, tris(dimethylamino)sulfonium difluorotrimethylsilicate, and/or ammonium fluoride but is not limited thereto.

The third intermediate may be for example represented by one of Chemical Formulae 6a to 6d.

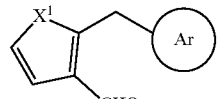

[Chemical Formula 6a]

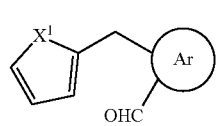

[Chemical Formula 6b]

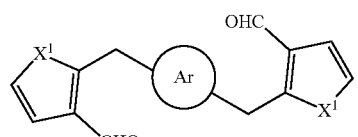

[Chemical Formula 6c]

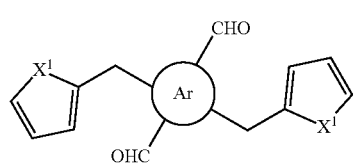

[Chemical Formula 6d]

In Chemical Formulae 6a to 6d,

Ar is one of a substituted or unsubstituted aromatic ring, a substituted or unsubstituted heteroaromatic ring, and a fused ring of the foregoing two or more rings, for example benzene, thiophene, selenophene, tellurophene, furan, pyrrole, and a fused ring of the foregoing two or more rings, and $X^1$ is O, S, Se, or Te.

The third intermediate may be formed into a fused heteroaromatic compound through a catalytic cyclization reaction. Herein, any catalyst used for a dehydration reaction, for example, an acidic catalyst may be used.

The each step may be performed in a solvent, and the solvent may be, for example an aliphatic hydrocarbon solvent (e.g., hexane, heptane, and methylene chloride); an aromatic hydrocarbon solvent (e.g., benzene, toluene, pyridine, quinoline, anisole, mesitylene, and xylene; a ketone-based solvent (e.g., methyl isobutyl ketone, 1-methyl-2-pyrrolidinone (NMP), cyclohexanone, and acetone); an ether-based solvent (e.g., tetrahydrofuran and isopropyl ether); an acetate-based solvent (e.g., ethyl acetate, butyl acetate, and propylene glycol methyl ether acetate); an amide-based solvent (e.g., dimethyl acetamide and dimethyl formamide (DMF)); a nitrile-based solvent (e.g., acetonitrile and benzonitrile); and a mixture of the solvents, but is not limited thereto.

The fused heteroaromatic compound may be for example represented by Chemical Formula 7 or 8.

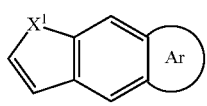

[Chemical Formula 7]

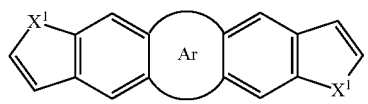

[Chemical Formula 8]

In Chemical Formulae 7 and 8,

Ar is a substituted or unsubstituted aromatic ring, a substituted or unsubstituted heteroaromatic ring, and a fused ring of the foregoing two or more rings, for example benzene, thiophene, selenophene, tellurophene, furan, pyrrole, and a fused ring of the foregoing two or more rings, and $X^1$ is O, S, Se, or Te.

The fused heteroaromatic compound has, for example a structure where three or more aromatic rings and/or heteroaromatic rings are fused, and has a uniform and stable oxidation potential when applied to an electronic device, e.g., an organic thin film transistor, due to a compact planar molecular structure, and shows relatively high charge mobility since the intermolecular packing and stacking are improved. Therefore, the fused heteroaromatic compound may be effectively applied to an electron transporting material, e.g., a semiconductor.

The fused heteroaromatic compound may have, for example a structure where four or more aromatic rings and/or heteroaromatic rings may be fused, five or more aromatic rings and/or heteroaromatic rings may be fused, six or more aromatic rings and/or heteroaromatic rings may be fused, seven or more aromatic rings and/or heteroaromatic rings may be fused, or eight or more aromatic rings and/or heteroaromatic rings may be fused.

The fused heteroaromatic compound may have, for example, a molecular weight of about 300 to about 3000, or about 300 to about 1500.

The fused heteroaromatic compound may be, for example, one of the following compounds, but is not limited thereto.

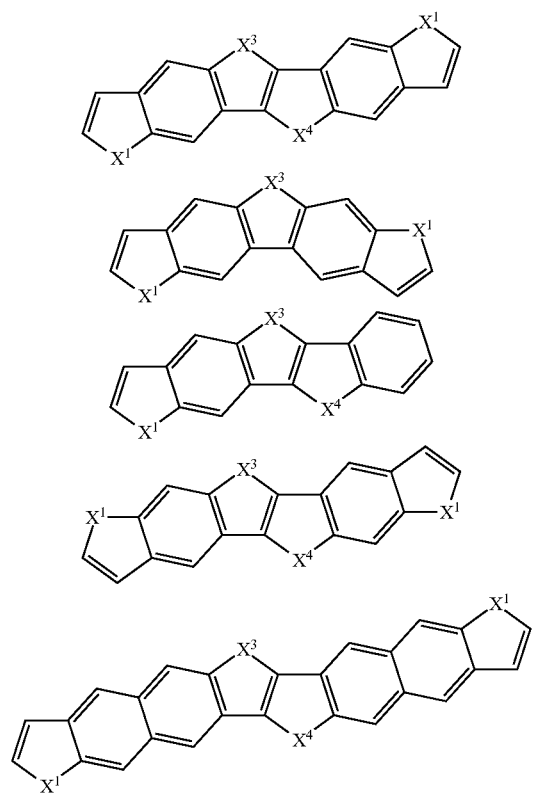

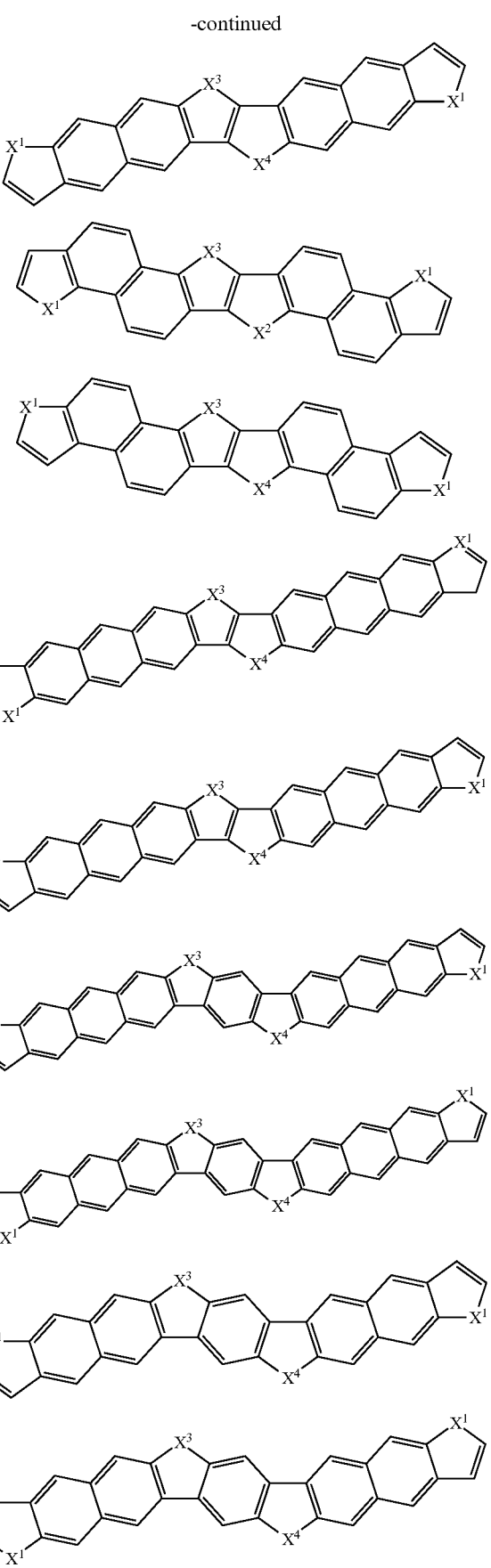

-continued

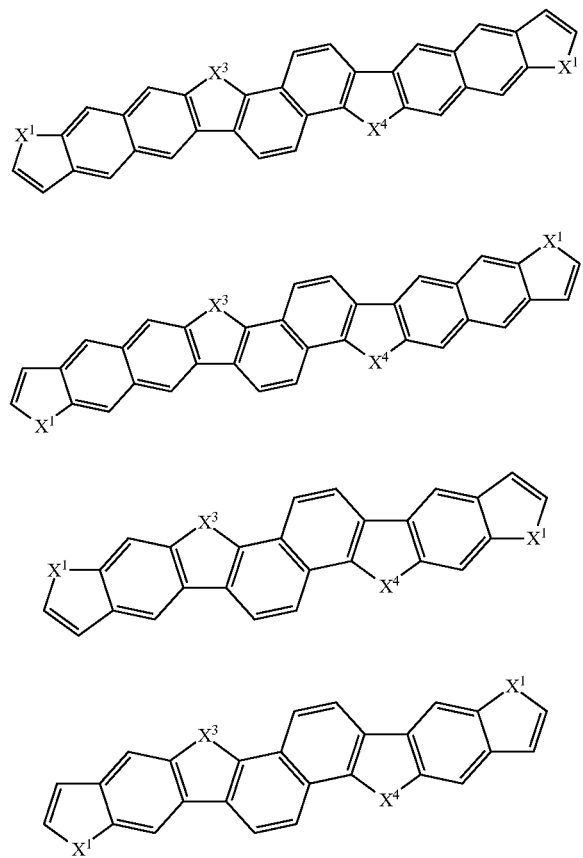

Herein, $X^1$ is O, S, Se, or Te, and $X^3$ and $X^4$ are independently O, S, Se, Te or NR' (R' is hydrogen, a C1 to C10 alkyl group or a C6 to C30 aryl group).

The synthetic method of a fused heteroaromatic compound may easily provide a fused heteroaromatic compound having unsubstituted thiophene, selenophene, furan, or tellurophene at the terminal end. Particularly, the fused heteroaromatic compound having unsubstituted selenophene at the terminal end, which is limited in a conventional method, may be easily obtained.

The synthetic method of a fused heteroaromatic compound may have each relatively simple synthesis step and may provide a product with a high yield. The synthetic method may be performed at a relatively low temperature of, for example about 40° C. to about 200° C., for example about 40° C. to about 100° C. The synthetic method may be performed at a relatively short time, and may shorten a time of a conventional method. The synthetic method may provide intermediates and a final product with a high yield, and for example each intermediate and final product may be produced with a yield of about 70% or more, for example about 70% or more.

The fused heteroaromatic compound may be implemented into an organic thin film by a deposition or solution process. The organic thin film may be applied to various devices including an organic semiconductor. For example, the fused heteroaromatic compound may be applied to an organic thin film transistor, and may be applied to a charge transport layer and/or an active layer of an electronic device, e.g., a solar cell, an organic light emitting diode (OLED) display, and an organic sensor.

Hereinafter, one example of an organic thin film transistor including the fused heteroaromatic compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view of an organic thin film transistor according to example embodiments.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material. Examples of the organic material may include a soluble polymer compound, e.g., a polyvinyl alcohol-based compound, a polyimide-based compound, a polyacryl-based compound, a polystyrene-based compound, and benzocyclobutane (BCB), and examples of the inorganic material may include a silicon nitride (SiNx) and a silicon oxide ($SiO_2$).

A source electrode 173 and a drain electrode 175 are formed on the gate insulating layer 140. The source electrode 173 and the drain electrode 175 face each other with the gate electrode 124 therebetween. The source electrode 173 is electrically connected to the data line (not shown) transferring the data signal. The source electrode 173 and the drain electrode 175 may include at least one metal selected from gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the fused heteroaromatic compound. The organic semiconductor 154 may be formed in a solution process, e.g., spin coating, slit coating, or inkjet printing, by preparing the fused heteroaromatic compound as a solution. However, the fused heteroaromatic compound may be formed using a dry process, e.g., deposition.

Although the bottom gate structured organic thin film transistor is illustrated as an organic thin film transistor, it is not limited thereto, and it may be applied to all organic thin film transistors, e.g., a top gate structured organic thin film transistor.

The organic thin film transistor may be applied to a switch or driving device of various electronic devices, and the electronic device may be, for example, a liquid crystal display (LCD), an organic light emitting diode (OLED) display, an electrophoretic display device, or an organic sensor.

Hereinafter, the present disclosure is illustrated in more detail with reference to examples. However, these are examples, and the present disclosure is not limited thereto.

Synthesis of Fused Heteroaromatic Compound

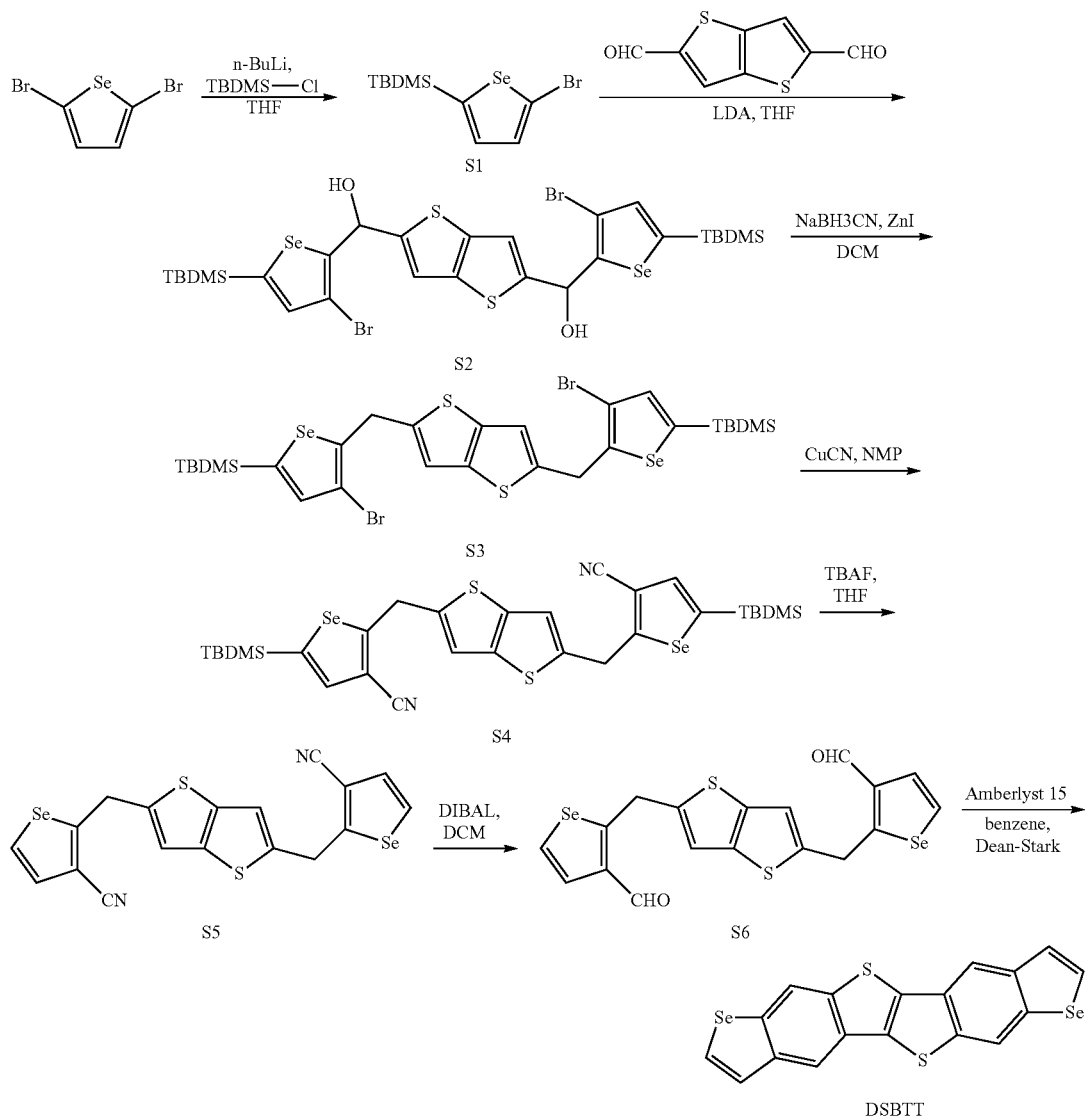

Synthesis of S1 Compound 15.0 g (52 mmol) of 2,5-dibromoselenophene is put in 400 ml of tetrahydrofuran to prepare a cool solution (−78° C.), n-butyllithium (2.5 M in hexane, 21 mL, 1 eq.) is added to the solution, and the reaction mixture is fervently stirred for 20 minutes. Subsequently, 7.8 g (52 mmol, 1 eq.) of t-butyldimethylsilylchloride is added thereto. Then, the reaction mixture is stirred at −78° C. all through the night, diluted with hexane, and several times cleaned with water and brine. Subsequently, an organic layer therefrom is dried with magnesium sulfate and evaporated to obtain 15.7 g of a S1 compound as a yellow liquid. The yield is 93.0%.

1H-NMR (300 MHz, CDCl3): δ 7.30 (d, J=3.6 Hz, 1H), 7.21 (d, J=3.6 Hz, 1H), 0.92 (m, 9H), 0.28 (m, 6H), 13C-NMR (75.5 MHz, CDCl3): 148.7, 137.8, 134.6, 120.1, 26.5, 16.9;

HRMS (m/z): [M]+ calcd for C10H17BrSeSi 323.9448; found: 323.9458.

Synthesis of S2 Compound 9.3 g (29 mmol, 2 eq.) of the S1 compound is put in 500 ml of dry tetrahydrofuran to prepare a cool solution (−78° C.), lithium diisopropylamide (2.0 M in THF/heptane/ethylbenzene, 15 mL, 2.1 eq.) is added thereto, and the reaction mixture is fervently stirred at −78° C. for 2 hours. Subsequently, thieno[3,2-B]thiophene-2,5-dialdehyde (2.8 g, 1 eq.) is added thereto, the mixture is stirred at room temperature all through night, and a sat. sodium bicarbonate solution is added thereto. Then, the solution is diluted with dichloromethane and several times cleaned with water, and an organic layer therefrom is dried with magnesium and evaporated to obtain a brown solid. Subsequently, the brown solid is recrystallized with a mixed solvent of ethylacetate/hexane/chloroform to obtain 6.7 g of an S2 compound as an ivory solid. The yield is 56.0%.

1H-NMR (300 MHz, CDCl3): δ 7.34 (s, 2H), 7.21 (s, 2H), 6.35 (s, 2H), 2.76 (d, J=2.1 Hz, 2H), 0.92 (m, 18H) 0.26 (m,

12H); 13C-NMR (125.8 MHz, CDCl3): 152.0, 148.4, 146.0, 140.3, 138.7, 118.3, 110.5, 71.0, 26.9, 17.4;

Synthesis of S3 Compound 9.1 g (10.8 mmol) of the S2 compound is put in 750 ml of dichloromethane to prepare a stirred solution, and 11.0 g (3.2 eq.) of zinc (II) iodide and 9.5 g (14.0 eq.) of sodium cyanoborohydride ($NaBH_3CN$) are slowly added thereto at 0° C. Subsequently, the reaction mixture is stirred for 24 hours, and a sat. ammonium chloride solution is added thereto. Then, the resulting material is diluted with dichloromethane and several times with water, and an organic layer therefrom is passed through a silica column and then, dried with magnesium sulfate and evaporated to obtain a solid. Subsequently, the solid is recrystallized with a mixed solvent of hexane and acetone to obtain 6.65 g of an S3 compound as an ivory solid. The yield is 76%.

1H-NMR (300 MHz, CDCl3): δ 7.34 (s, 2H), 7.03 (s, 2H), 4.37 (s, 4H), 0.91 (m, 18H), 0.23 (m, 12H); 13C-NMR (125.8 MHz, CDCl3): 147.7, 143.9, 143.2, 139.8, 137.6, 118.1, 111.2, 33.2, 26.3, 16.8, −4.8; HRMS (m/z): [M]+ calcd for C28H38Br2S2Se2Si2 813.8630; found: 813.8409.

Synthesis of S4 Compound

A mixture of 1 g (1.23 mmol) of the S3 compound and 0.35 g (3.2 eq.) of copper (I) cyanide (CuCN) is put in 15 ml of N-methyl-2-pyrrolidone, and the mixture is 15 times repetitively radiated at 180° C. with 30 W for 80 minutes by using a microwave reactor. Subsequently, the reaction solution is diluted with water and filtered, and the water and the N-methyl-2-pyrrolidone are removed therefrom. The obtained powder is dissolved in dichloromethane and several times cleaned with water. Subsequently, an organic layer therefrom is dried with magnesium sulfate and evaporated to obtain 9.8 g of an S4 compound as a brown solid. The yield is 75%.

1H-NMR (300 MHz, CDCl3): δ 7.51 (s, 2H), 7.10 (s, 2H), 4.60 (s, 4H), 0.90 (m, 18H), 0.25 (m, 12H); 13C-NMR (125.8 MHz, CDCl3): 167.6, 146.7, 142.5, 137.9, 137.2, 118.7, 115.9, 112.6, 33.0, 26.2, 16.6, −4.8; HRMS (m/z): [M]+ calcd for C30H38N2S2Se2Si2 706.0345; found: 706.0318.

Synthesis of S5 Compound 23 g (32.6 mmol) of the S4 compound is put in 700 ml of tetrahydrofuran to prepare a stirred solution, 35 ml (1.1 eq.) of a tetrabutylammonium fluoride solution (1 M in tetrahydrofuran) is added thereto at 0° C. Subsequently, the reaction mixture is stirred for 30 minutes and cooled down with water. Then, a resulting material obtained therefrom is diluted with dichloromethane and several times cleaned with water. Subsequently, an organic layer therefrom is dried with magnesium sulfate and evaporated under vacuum. Then, a product therefrom is purified through column chromatography using silica gel (chloroform:hexane, 3:1) to obtain 9.8 g of an S5 compound as a light yellow solid. The yield is 63%.

1H-NMR (300 MHz, CDCl3): δ 7.91 (d, J=5.4 Hz, 2H), 7.37 (d, J=5.4 Hz, 2H), 7.11 (s, 2H), 4.60 (s, 4H); 13C-NMR (125.8 MHz, CDCl3): 163.3, 142.6, 138.0, 130.9, 130.0, 118.7, 115.6, 111.1, 32.9 HRMS (m/z): [M]+ calcd for C18H10N2S2Se2 477.8616; found: 477.8438.

Synthesis of S6 Compound 5.4 g (11.3 mmol) of the S5 compound is put in 1000 ml of dichloromethane to prepare a stirred solution, and 50 ml (4.4 eq.) of a diisobutylaluminum hydride solution (1.0 M in tetrahydrofuran) is added thereto at 0° C. Subsequently, the reaction mixture is stirred for 30 minutes and cooled down with a mixed solution of methanol and 1N hydrochloric acid (2:1 v/v). Then, a resulting material therefrom is diluted with dichloromethane and several times cleaned with water, and then, an organic layer is dried with magnesium sulfate and evaporated to obtain a brown solid. The solid is recrystallized with chloroform to obtain 5.1 g of an S6 compound as an ivory solid. The yield is 93%.

1H-NMR (300 MHz, CDCl3): δ 10.06 (s, 2H), 7.84 (d, J=5.7 Hz, 2H), 7.68 (d, J=5.7 Hz, 2H), 7.06 (s, 2H), 4.83 (s, 4H); 13C-NMR (125.8 MHz, CDCl3): 184.7, 164.0, 143.6, 139.0, 137.8, 130.5, 129.1, 118.5, 31.8 HRMS (m/z): [M]+ calcd for C18H10N2S2Se2 477.8616; found: 477.8438.

Synthesis of Fused Heteroaromatic Compound (DSBTT)

5.1 g (10.5 mmol) of the S6 compound is put in 350 ml of dry benzene to prepare a stirring solution, and 12.0 g of Amberlyst 15 is added thereto under a nitrogen atmosphere. Subsequently, the obtained solution is refluxed all through night and then, cooled down to room temperature. Then, a floating material is filtered to obtain a gray solid, DSBTT. The gray solid is additionally sublimed to manufacture a device and perform an X-ray crystalline analysis.

UV/Vis: A $λ_{edge}$ 417 nm; HRMS (m/z): [M]+ calcd for C18H8S2Se2 447.840; found: 447.946.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A compound represented by Chemical Formula 1 or 2:

[Chemical Formula 1]
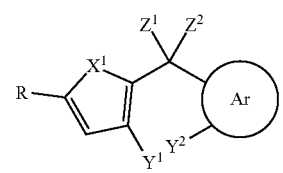

[Chemical Formula 2]
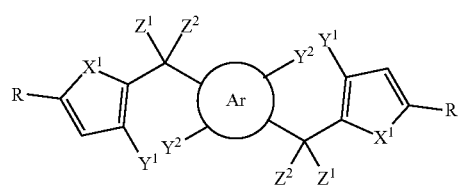

wherein, in Chemical Formulae 1 and 2,

Ar is benzene, thiophene, selenophene, tellurophene, furan, pyrrole, or a fused ring of the foregoing two or more rings, $X^1$ is Se or Te, each of $Y^1$ and $Y^2$ is hydrogen or halogen, wherein one of $Y^1$ and $Y^2$ is a halogen and another of $Y^1$ and $Y^2$ is hydrogen, each of $Z^1$ and $Z^2$ are hydrogen or a hydroxy group, and R is a protective group, the protective group consists of a substituted or unsubstituted silyl group.

2. The compound of claim 1, wherein the protective group is a trimethylsilyl group, a triethylsilyl group, an isopropyldimethylsilyl group, a diethylisopropylsilyl group, a t-butyldimethylsilyl group, a t-butyldiphenylsilyl group, or a triisopropylsilyl group.

* * * * *